United States Patent
Kennedy et al.

(10) Patent No.: US 7,640,810 B2
(45) Date of Patent: Jan. 5, 2010

(54) ULTRASONIC INSPECTION APPARATUS, SYSTEM, AND METHOD

(75) Inventors: James C. Kennedy, Renton, WA (US); Mark L. Little, Auburn, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 374 days.

(21) Appl. No.: 11/178,584

(22) Filed: Jul. 11, 2005

(65) Prior Publication Data

US 2007/0006658 A1 Jan. 11, 2007

(51) Int. Cl.
*G01N 29/265* (2006.01)
(52) U.S. Cl. .......................................... 73/634; 73/602
(58) Field of Classification Search .................. 73/634, 73/602
See application file for complete search history.

(56) References Cited

U.S. PATENT DOCUMENTS

| | | | | |
|---|---|---|---|---|
| 3,534,591 | A | * | 10/1970 | Phelan ........................ 73/634 |
| 3,575,042 | A | | 4/1971 | Lovelace et al. |
| 3,789,350 | A | | 1/1974 | Rolle |
| 3,809,607 | A | * | 5/1974 | Murray et al. ............... 376/249 |
| 3,958,451 | A | | 5/1976 | Richardson |
| 4,010,636 | A | | 3/1977 | Clark et al. |
| 4,103,234 | A | | 7/1978 | Frazier, Jr. |
| 4,117,733 | A | | 10/1978 | Gugel |
| 4,160,386 | A | | 7/1979 | Jackson et al. |
| 4,167,880 | A | | 9/1979 | George |
| 4,173,897 | A | | 11/1979 | Fostermann et al. |
| 4,173,898 | A | | 11/1979 | Fostermann et al. |
| 4,229,796 | A | | 10/1980 | Garrett |
| 4,311,052 | A | | 1/1982 | Jeffras et al. |
| 4,327,588 | A | | 5/1982 | North |
| 4,365,514 | A | | 12/1982 | Ho |

(Continued)

FOREIGN PATENT DOCUMENTS

DE 28 31 395 A1 1/1980

(Continued)

OTHER PUBLICATIONS

U.S. Appl. No. 10/943,088, filed Sep. 16, 2004; In re: Georgeson et al.; entitled *Magnetically Attracted Inspecting Apparatus and Method Using a Ball Bearing.*

(Continued)

*Primary Examiner*—Hezron Williams
*Assistant Examiner*—Rose M Miller
(74) *Attorney, Agent, or Firm*—Alston & Bird LLP

(57) ABSTRACT

Improved apparatus, systems, and methods for inspecting a structure are provided that use a pedestal robot mounted on a rail system, a probe extension coupler, and an inspection probe capable of performing pulse echo ultrasonic inspection. A probe may also include sled appendages and an axial braking system to inspect over holes and off edges. A probe may also include an ultrasonic pulse echo transducer array for high rate inspection; the transducer array may be mounted in a bubbler shoe for individually coupling each of the transducers in the array. A rail system may also include an optical encoder for providing location information for the robot and axial braking system. A probe extension coupler presses the inspection probe against the structure for adjusting to changes in surface contours.

20 Claims, 8 Drawing Sheets

U.S. PATENT DOCUMENTS

| | | | |
|---|---|---|---|
| 4,368,644 A | 1/1983 | Wentzell et al. | |
| 4,399,703 A | 8/1983 | Matzuk | |
| 4,466,286 A | 8/1984 | Berbeé et al. | |
| 4,470,304 A | 9/1984 | Nusbickel, Jr. et al. | |
| 4,474,064 A | 10/1984 | Naruse et al. | |
| 4,495,587 A * | 1/1985 | Plante et al. | 702/38 |
| 4,559,825 A | 12/1985 | Martens | |
| 4,612,808 A | 9/1986 | McKirdy et al. | |
| 4,752,895 A | 6/1988 | Sarr | |
| 4,755,953 A | 7/1988 | Geithman et al. | |
| 4,774,842 A | 10/1988 | Kollar | |
| 4,803,638 A | 2/1989 | Nottingham et al. | |
| 4,807,476 A | 2/1989 | Cook et al. | |
| 4,848,159 A | 7/1989 | Kennedy et al. | |
| 4,912,411 A | 3/1990 | Allison et al. | |
| 5,007,291 A | 4/1991 | Walters et al. | |
| 5,047,771 A | 9/1991 | Engeler et al. | |
| 5,050,703 A | 9/1991 | Graff et al. | |
| 5,062,301 A | 11/1991 | Aleshin et al. | |
| 5,148,414 A | 9/1992 | Graff et al. | |
| 5,164,921 A | 11/1992 | Graff et al. | |
| 5,241,135 A | 8/1993 | Fetzer | |
| 5,396,890 A | 3/1995 | Weng | |
| 5,417,218 A | 5/1995 | Spivey et al. | |
| 5,421,203 A | 6/1995 | Graff et al. | |
| 5,485,084 A | 1/1996 | Duncan et al. | |
| 5,535,628 A | 7/1996 | Rutherford | |
| 5,567,881 A | 10/1996 | Myers | |
| 5,585,564 A | 12/1996 | Brunty et al. | |
| 5,593,633 A | 1/1997 | Dull et al. | |
| 5,621,414 A | 4/1997 | Nakagawa | |
| 5,677,490 A | 10/1997 | Gunther et al. | |
| 5,698,787 A | 12/1997 | Parzuchowski et al. | |
| 5,786,535 A | 7/1998 | Takeuchi et al. | |
| 5,902,935 A | 5/1999 | Georgeson et al. | |
| 5,963,882 A | 10/1999 | Viertl et al. | |
| 5,986,549 A | 11/1999 | Teodorescu | |
| 6,057,927 A | 5/2000 | Levesque et al. | |
| 6,167,110 A | 12/2000 | Possin et al. | |
| 6,220,099 B1 | 4/2001 | Marti et al. | |
| 6,474,164 B1 | 11/2002 | Mucciardi et al. | |
| 6,484,583 B1 | 11/2002 | Chennell et al. | |
| 6,507,635 B2 | 1/2003 | Birdwell et al. | |
| 6,516,668 B2 | 2/2003 | Havira et al. | |
| 6,641,535 B2 | 11/2003 | Buschke et al. | |
| 6,658,939 B2 | 12/2003 | Georgeson et al. | |
| 6,711,235 B2 | 3/2004 | Galish et al. | |
| 6,722,202 B1 | 4/2004 | Kennedy et al. | |
| 6,725,721 B2 | 4/2004 | Venczel | |
| 6,748,791 B1 | 6/2004 | Georgeson et al. | |
| 6,772,635 B1 | 8/2004 | Sale et al. | |
| 6,829,959 B2 | 12/2004 | Gifford et al. | |
| 6,839,636 B1 | 1/2005 | Sunshine et al. | |
| 6,843,130 B2 | 1/2005 | Georgeson | |
| 6,843,131 B2 | 1/2005 | Graff et al. | |
| 6,843,312 B2 | 1/2005 | Burk et al. | |
| 6,848,312 B2 | 2/2005 | Georgeson | |
| 6,895,079 B2 | 5/2005 | Birdwell et al. | |
| 6,927,560 B2 | 8/2005 | Pedigo et al. | |
| 6,931,931 B2 | 8/2005 | Graff et al. | |
| 7,050,535 B2 | 5/2006 | Georgeson et al. | |
| 7,064,332 B2 | 6/2006 | Favro et al. | |
| 7,228,741 B2 | 6/2007 | Georgeson et al. | |
| 7,231,826 B2 | 6/2007 | Bossi et al. | |
| 7,240,556 B2 | 7/2007 | Georgeson et al. | |
| 7,249,512 B2 | 7/2007 | Kennedy et al. | |
| 7,253,908 B2 | 8/2007 | Vaccaro et al. | |
| 7,263,889 B2 | 9/2007 | Kennedy et al. | |
| 2003/0192382 A1 | 10/2003 | Mueller | |
| 2006/0243051 A1 | 11/2006 | Bui et al. | |
| 2007/0044563 A1 | 3/2007 | Sarr et al. | |
| 2007/0044564 A1 | 3/2007 | Bui et al. | |

FOREIGN PATENT DOCUMENTS

| | | | |
|---|---|---|---|
| DE | 28 52 560 B1 | | 1/1980 |
| DE | 4431625 C1 | * | 3/1996 |
| DE | 198 26 759 C1 | | 12/1999 |
| DE | 100 43 199 A1 | | 9/2002 |
| EP | 1 193 491 A2 | | 4/2002 |
| JP | 62245153 A | * | 10/1987 |
| JP | 05346487 A | * | 12/1993 |
| JP | 09 264877 A | | 10/1997 |
| WO | WO 2004106802 A1 | * | 12/2004 |

OTHER PUBLICATIONS

U.S. Appl. No. 10/943,135, filed Sep. 16, 2004; In re: Georgeson et al.; entitled *Magnetically Attracted Inspecting Apparatus and Method Using a Fluid Bearing*.

U.S. Appl. No. 11/178,637, filed Jul. 11, 2005; In re: Kennedy et al.; entitled *Ultrasonic Array Probe Apparatus, System, and Method for Traveling Over Holes and Off Edges of a Structure*.

fischertechnik, Pneumatic Robots, Pneumatic Information; http://www.mbhs.edu/~josborn/palmbot/Info_eng.pdt, available Oct. 10, 2005, pp. 1-5.

FANUC robotics, R-2000iA Series: http://www.fanucrobotics.com/file_repository/fanucmain/R-2000iA%20Series.pdf, available Oct. 10, 2005, 4 pages.

ABB IRB 6600: http://www.abb.co.in/global/inabb/inabb509.nsf/0/579e92967cad8bd16525703b00306b3e/$file/Robotics+IRB6600.pdf; available Oct. 10, 2005, 2 pages.

*CL—Concentric Lock—Pillow Blocks*, http://www.qmbearing.com/CLPillowBlock.html; available Apr. 6, 2005; 2 pages.

*Airpel Anti-Stiction Cylinders*; http://www.airpot.com/beta/html/airpel.html; available Apr. 11, 2005, 2 pages.

* cited by examiner

ULTRASONIC INSPECTION APPARATUS, SYSTEM, AND METHOD

CROSS-REFERENCE TO RELATED APPLICATIONS

The contents of U.S. Pat. No. 6,722,202; U.S. Pat. No. 7,231,826; U.S. Patent Application Publication 2006/0055399; U.S. Pat. No. 7,320,249; and U.S. Pat. No. 7,337,673 are incorporated by reference.

FIELD OF THE INVENTION

The present invention relates generally to an apparatus, system, and method for inspecting a structure and, more particularly, to an apparatus, system, and method for non-destructive pulse echo ultrasonic inspection of a structure and inspection near holes and edges of the structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors are typically used to provide indications of voids or porosity, such as in adhesive bondlines of the structure. High resolution inspection of aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. However, it has traditionally not always been possible to perform continuous scanning of a structure with holes and off the edges of the structure. For example, inspection probes which contact and ride along the surface of the structure under inspection and are typically supported against the structure by the pull of gravity or by pressure exerted by a motion control system, referred to as part-riding probes, may fall through a hole in a structure or off the edge of the structure. Although a structure can be inspected in a manner to scan around holes, a second inspection method typically must be performed for inspecting the edges of the structure and edges defining holes in the structure. For example, a technician can manually scan around the edges of the structure and the edges of holes in a structure using a pulse-echo or through transmission ultrasonic hand probe.

Non-destructive inspection may be performed manually by technicians who typically move an appropriate sensor over the structure. Manual scanning requires a trained technician to move the sensor over all portions of the structure needing inspection. While manual scanning may be required around the edges of the structure and the edges of holes in a structure, manual scanning may also be employed for scanning the remainder of the structure.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections. It is often complicated, time consuming, and expensive to program and control an automated motion control system with respect to surface contours of a structure to within sufficient precision for performing inspection and maintaining consistent quality of inspection. The automated motion control system would have to make many small movements to keep an inspection probe riding on a contoured surface. For example, if the surface contour of a structure varies across a scanning area, an automated motion control system would need to both know the precise surface contour of the structure and be capable of moving an inspection probe over the surface of the structure while maintaining consistent orientation of the inspection probe with respect to the surface contours of the structure. The automated motion control system would have to be programmed for the shape, contours, and structural features of each structure to be inspected. Furthermore, variances in surface contours of the actual structure may not precisely match the data for the surface contours of the structure provided to the automated motion control system, thereby disturbing the automated motion control system's ability to maintain the inspection probe in consistent orientation with respect to the structure.

Accordingly, improved apparatus, systems, and methods for continuous inspection of structures with varying surface contours and features, such as large composite structures having surface curvature and including holes, and continuous inspection at edges of the structures are desired.

SUMMARY OF THE INVENTION

The present invention provides apparatus, systems, and methods for inspecting a structure using a motion control system, a probe extension coupler, and an inspection probe capable of performing pulse echo ultrasonic inspection. Apparatus, systems, and methods of the present invention provide the capability to non-destructively inspect large, contoured, composite structures with increased speed of inspection provided by a pedestal robot mounted on a rail system, an array of transducers, and a probe capable of scanning over holes and off edges of the structure.

For continuous scanning applications, embodiments of apparatus, systems, and methods of the present invention use a motion control system and an extension coupler to press a part-riding probe against the surface of the structure, typically using one or more sled appendages and axial and extension braking systems, thereby reducing the necessary sophistication of the motion control system to maintain the probe in a predefined orientation and predefined position with respect to the surface of the structure.

According to one aspect of the present invention, an apparatus, system, and method for non-destructive inspection of a structure includes a motion control system, a probe extension coupler, and an inspection probe capable of performing pulse echo ultrasonic inspection. A probe according to the present invention may include sled appendages, an axial braking system, and at least one pulse echo ultrasonic transducer to inspect over holes and off edges by being configured for traveling over a surface of the structure along the sled appendages, using the axial and extension braking systems for temporarily locking the position of the sled appendages when traveling over holes and off edges of the structure and using the ultrasonic transducer for inspecting the structure. A probe may include an array of ultrasonic pulse echo transducers for high rate inspection. If a couplant is used to couple the transducers to the surface of the structure, the transducer array may be mounted in a bubbler shoe for individually coupling each of the transducers in the array to prevent loss of coupling of transducers remaining over the surface of the structure when one or more transducers are over a hole or off an edge. A probe according to the present invention is also configured for riding along a curved surface of a structure under the control of a robotic arm and by way of an extension coupler, and advantageously operates to provide continuous scanning of a large structure when the robotic arm is mounted on a rail system. A motion control system according to the present invention may also include an optical encoder for providing location information for the robot and braking systems. A probe extension coupler according to the present invention presses the inspection probe against the structure to adjust for surface contour changes.

According to another aspect of the present invention, a method may include providing an ultrasonic inspection system for inspecting a structure, the ultrasonic inspection system having a motion control system, an extension coupler, and an inspection probe; moving the probe over the structure using the motion control system; pressing the probe to the structure using the extension coupler; transmitting pulse echo ultrasonic signals from the transducer into the structure; and receiving pulse echo ultrasonic signals at the transducer reflected from the structure.

Embodiments of apparatus, systems, and methods of the present invention typically operate in array modes using an array of pulse echo ultrasonic transducers, thereby increasing inspection speed and efficiency while reducing cost. Apparatus, systems, and methods of the present invention are also capable of operating with a single or a plurality of pulse echo ultrasonic transducers.

BRIEF DESCRIPTION OF THE DRAWING(S)

DETAILED DESCRIPTION

Figure 1:
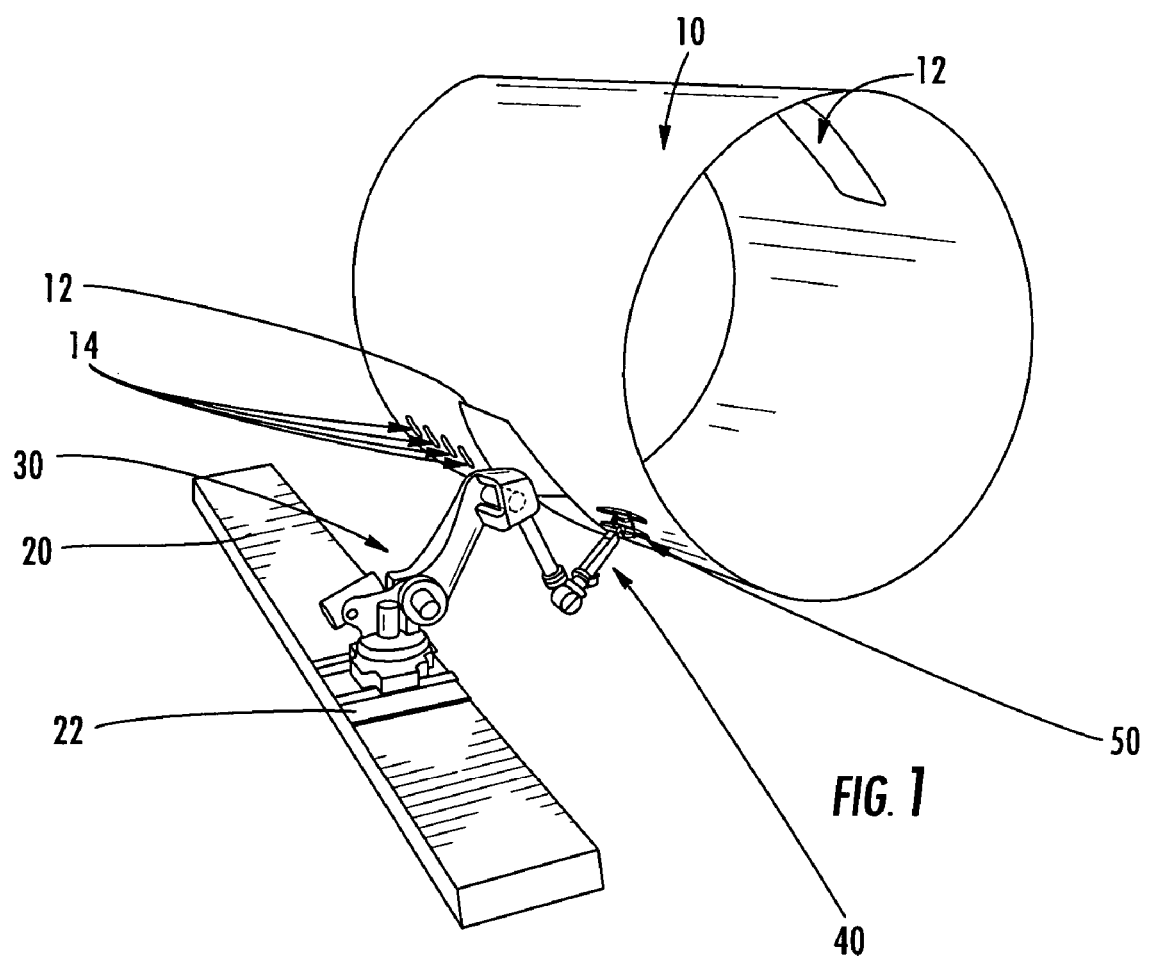
FIG. 1 is a diagram of an embodiment of an ultrasonic inspection system of the present invention.

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

The term "motion control system" refers generally to a system which provides motion and control (controlled motion) to another device, such as an attached inspection probe, extension coupler, drilling apparatus, or other device attached to a distal end of the motion control system. A motion control system may include one or more subsystems, such as a rail system or a robot motion control system. A motion control system may include a controller, such as a computer or similar hardware and/or software device, for issuing electronic signals to command the controlled motion of the motion control system. A subsystem of a motion control system may similarly include a controller to command the subsystem. A controller of a motion control system may be capable of communicating with a controller of a subsystem to cooperatively command the subsystem, or a controller of a motion control system may be independently capable of commanding one or more subsystems of the motion control system. The term "robot motion control system" refers generally to an automated device which includes a robotic arm that provides at least one direction or degree of motion, but typically provides as many as four to six degrees of motion.

The term "holes" refers to holes of varying sizes in a structure, including features described as "cut-outs" in the structure. The term "edges" refers generally to the sides of the structure, but also includes reference to the perimeter of holes, particularly large holes or cut-outs through which a conventional part-riding probe might fall through. Thus, holes may be described as having edges, and the term edges is inclusive of both an external perimeter of a structure and perimeters of internal holes in the structure. Although being characteristically different, for purposes of the present invention holes and edges differ primarily by the manner in which a probe operates near these features. For example, the probe typically travels over a hole or cut-out but travels off an edge of the structure, and possibly returning over the structure from an edge. Further, while in some instances in the description below using only one of the two terms holes and edges may be sufficient, typically both terms are used to emphasize that the described function or operation applies to both holes in the structure and edges of the structure, and not merely one of these features.

The term "rotatably" refers to a characteristic of angular motion in at least one plane, and typically only one plane as may be defined by a connection about an axis-line as described in the examples below. However, a rotatable connection may also be defined by a connection that provides angular motion in more than one plane, such as a ball-and-socket joint connection that permits motion of the joint without permitting rotation in at least one plane, such as to provide freedom of motion to pitch and roll, but not yaw.

An embodiment of an ultrasonic inspection apparatus, system, or method of the present invention may be used to inspect a variety of structures, such as those described above and including composite structures of a wide range of sizes and shapes, such as composite aircraft wings and fuselage barrels. While embodiments of the present invention may be particularly useful for performing non-destructive inspection of large, contoured, composite structures that include holes or cut-outs, collectively referred to herein as holes, embodiments of ultrasonic inspection apparatus and systems of the present invention may also be used for non-destructive inspection of smaller structures and/or flat structures. Embodiments of apparatus, systems, and methods of the present invention can be used for inspection of structures during manufacture or in-service.

The present invention provides apparatus, systems, and methods for inspecting a structure using a motion control system, a probe extension coupler, and an inspection probe capable of performing pulse echo ultrasonic inspection, including inspecting large, contoured structures and inspecting over holes and off edges of structures. Several discrete components are combined to form an ultrasonic inspection apparatus or system of the present invention. For example, a pedestal robot mounted on a rail system may be included in a motion control system. A dual action pneumatic cylinder, such as an Airpel® E9 D1200 anti-stiction cylinder from Airpot Corporation of Norwalk, Conn., with a corresponding support structure may be included in an extension coupler. And a probe with an array of pulse echo ultrasonic transducers, sled appendages, and an axial braking system may be included in a probe.

Apparatus, systems, and methods of the present invention provide the capability to non-destructively inspect large, contoured, composite structure with increased speed of inspection using a pedestal robot mounted on a rail system, an array of transducers, and a probe capable of scanning over holes and off edges of the structure. A probe according to the present invention may include sled appendages and an axial braking system to inspect over holes and off edges. A probe may also include at least one pulse echo ultrasonic transducer, but typically includes an array of pulse echo ultrasonic transducers for high rate inspection. If a couplant is used to couple the transducers to the surface of the structure, the transducer array may be mounted in a bubbler shoe for individually coupling each of the transducers in the array to prevent loss of coupling of transducers remaining over the surface of the structure when one or more transducers are over a hole or off an edge. A probe according to the present invention is also configured for riding along a curved surface of a structure under the control of a robotic arm and by way of an extension coupler, and advantageously operates to provide continuous scanning of a large structure when the robotic arm is mounted on a rail system. A motion control system according to the present invention may also include an optical encoder for providing location information for the robot and axial braking system. A probe extension coupler according to the present invention presses the inspection probe against the structure for adjusting to changes in surface contours.

Many structures requiring non-destructive inspection are contoured, such as large and thin graphite structures. Surface contour changes in these structures often are not precisely defined in three-dimensions for referenced motion by a motion control system, such as a pedestal robot. However, using an embodiment of an ultrasonic inspection system of the present invention, a motion control system may be programmed to merely move an inspection probe and extension coupler over a general shape of the structure for scanning, but not precisely adjust for surface contour changes to maintain transducers of the inspection probe in constant orientation with respect to the contoured surface. Rather, by allowing the probe to ride across the structure and having the extension coupler press the probe against the structure, the motion control system need only move the probe and extension coupler over the structure for inspection and does not need to adjust for surface contour changes. The extension coupler pressing the probe against the surface and the freedom of motion of the probe compensate for surface contour changes, thereby, overcoming unknown and/or un-programmed variations in the surface of the structure. Freedom of motion of an inspection probe is typically achieved by rotatably connecting the sled appendages on which the probe rides over the surface of the structure. Contact with the surface ensures consistent orientation of transducers with respect to the structure for pulse echo ultrasonic inspection. Contact with the surface also permits accurate position measurement of the inspection device during continuous scanning, such as keeping an optical or positional encoder in physical and/or visual contact with the surface of the structure under inspection. Contact with the surface also permits the probe to disperse a couplant between the surface of the structure and the pulse echo ultrasonic transducers. Thus, an embodiment of an ultrasonic inspection program may use a low-cost, commercial, industrial robot as part of the motion control system without requiring programming the motion control system for controlling precise motion of an inspection probe to maintain constant orientation with the surface of a structure. Rather, the motion control system may be programmed merely to scan the structure, or a section of the structure, without compensating for surface contour variations or merely compensating for the overall shape of the structure and gross changes in surface contours. For example, to inspect a fuselage barrel with a nineteen foot diameter, a motion control system of an embodiment of an ultrasonic inspection system of the present invention may move back and forth to scan a five-foot perimeter rectangular scan area, allowing an extension coupler and an inspection probe according to the present invention to compensate for changes in the surface contour. The entire fuselage barrel can be inspected by scanning five-foot perimeter rectangular scan areas and rotating the fuselage barrel by 30°. An extension coupler between the motion control system and the inspection probe adjusts for surface contour variations. The extension coupler allows the probe to extend and retract with, typically, as much as one foot of z-axis travel, allowing the probe to move in and out one foot to compensate for the contour of the structure. Also, by allowing the probe to ride on the surface of the structure, a probe is capable of using a large array of ultrasonic transducers, such as a four-by-four offset pattern of pulse echo ultrasonic transducers, to provide a high inspection rate and increased coverage for inspection.

Where a couplant is used, a probe may also include a bubbler shoe that disperses the couplant around each pulse echo ultrasonic transducer to independently couple the signal from each transducer to the surface of the part. By individually coupling each transducer to the surface of the part, the bubbler shoe compensates for when the probe travels over a hole or off an edge of the structure where all of the transducers are not over the surface of the structure. In such a manner, only the probes over the hole or off the edge of the structure will lose the coupling with the surface, but the transducers remaining over the surface of the structure will continue to be independently coupled.

An axial braking system of a probe may be used to fix the position of sled appendages for traveling over holes or off an edge of the structure. Thus, for continuous scanning applications, the probe contacts and rides along the surface of the structure on the sled appendages, but as the probe approaches a hole or edge, the axial braking system, either using data of the hole and edge positions for the structure and the current location of the probe or using braking signals from a motion control system, fixes the current position of the sled appendages for traveling over the hole or off an edge and again contacting and riding along the surface of the structure after passing the hole or retracting from the edge at which time the axial braking system releases to permit the sled appendages to follow the contour of the surface of the structure. An axial braking system of an embodiment of a probe according to the present invention can operate in more than one axis, and typically operates in two perpendicular axes referred to herein as the x-axis perpendicular to the distal length of the sled appendages to control the front-to-back tilt, or pitch, of the sled appendages and the y-axis parallel to the distal length of the sled appendages to control the side-to-side slant, or roll, of the sled appendages.

FIG. 1 is a diagram of an embodiment of an ultrasonic inspection system of the present invention. The system is capable of non-destructive inspection of a large, contoured, composite structure, such as a fuselage barrel 10 including door cut-outs 12 and window holes 14. The ultrasonic inspection system includes a motion control system having a robotic control system 30 mounted to a robot carriage 22 of a rail system. The term "robot carriage" refers to a portion of a rail system to which a robot motion control system is attached for being moved along the rail system. The rail system also includes structure 20 configured to provide translational motion of the robot carriage 22 over the length of the rail system. For example, the structure 20 may have a rack and pinion configuration, and the robot carriage 22 may include an electronic drive motor which operates a gear to translate the robotic control system 30 along the length of the rail system. A rail system may be mounted in any manner to provide translation of a robotic control system, including an overhead rail system, a wall-mounted rail system, and a ground positioned rail system. A robotic control system 30 may be any type of automated robotic motion control system mounted to the robot carriage 22, such as an R2000iA™ Series 6-Axis Robot from FANUC Robotics or an IRB 6600 Robot from ABB.

A probe extension coupler 40 may be attached to the distal end of the robotic arm of the robotic motion control system. The extension coupler 40 connects the motion control system with an inspection probe 50. An inspection probe 50 according to the present invention is capable of traveling over holes and off edges of a structure under inspection. For example, as the motion control system scans a longitudinal rectangular section of the perimeter of the fuselage barrel 10, the inspection probe 50 and extension coupler 40 may operate to prevent the inspection probe 50 from falling through a hole or cut-out 12, 14 or off the edge of the fuselage barrel 10. In such a manner, the combination of the motion control system, extension coupler, and inspection probe provide for inspection of large, contoured structures, such as a fuselage barrel 10, including structures requiring inspection over holes and at the edges of the structure.

Figure 2:
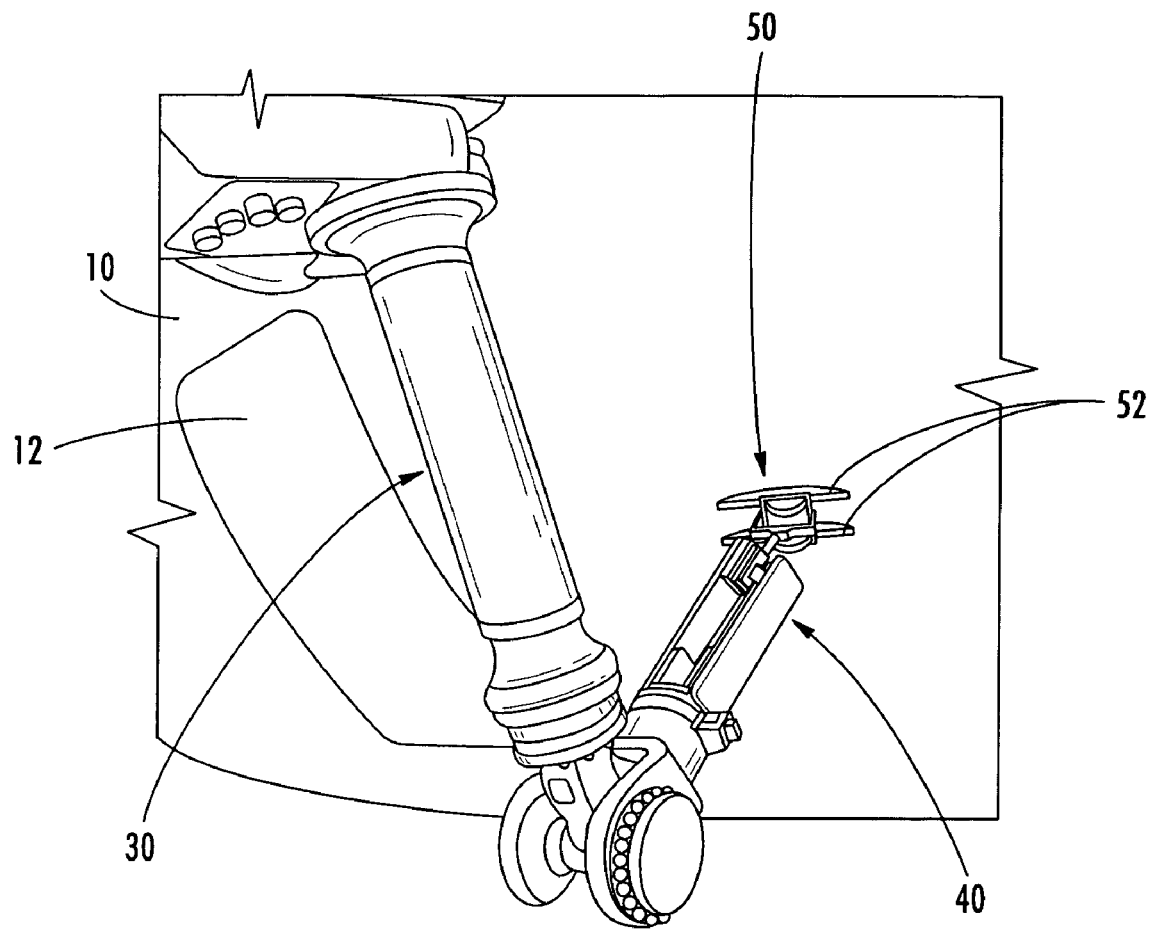
FIG. 2 is another view of the diagram of the ultrasonic inspection system of FIG. 1.

FIG. 2 provides another view of the diagram of the ultrasonic inspection system of FIG. 1, specifically providing a better view of embodiments for an extension coupler 40 and inspection probe 50 according to the present invention. An inspection probe 50 according to the present invention is further described in U.S. Pat. No. 7,337,673, the contents of which are hereby incorporated by reference.

Figure 3:
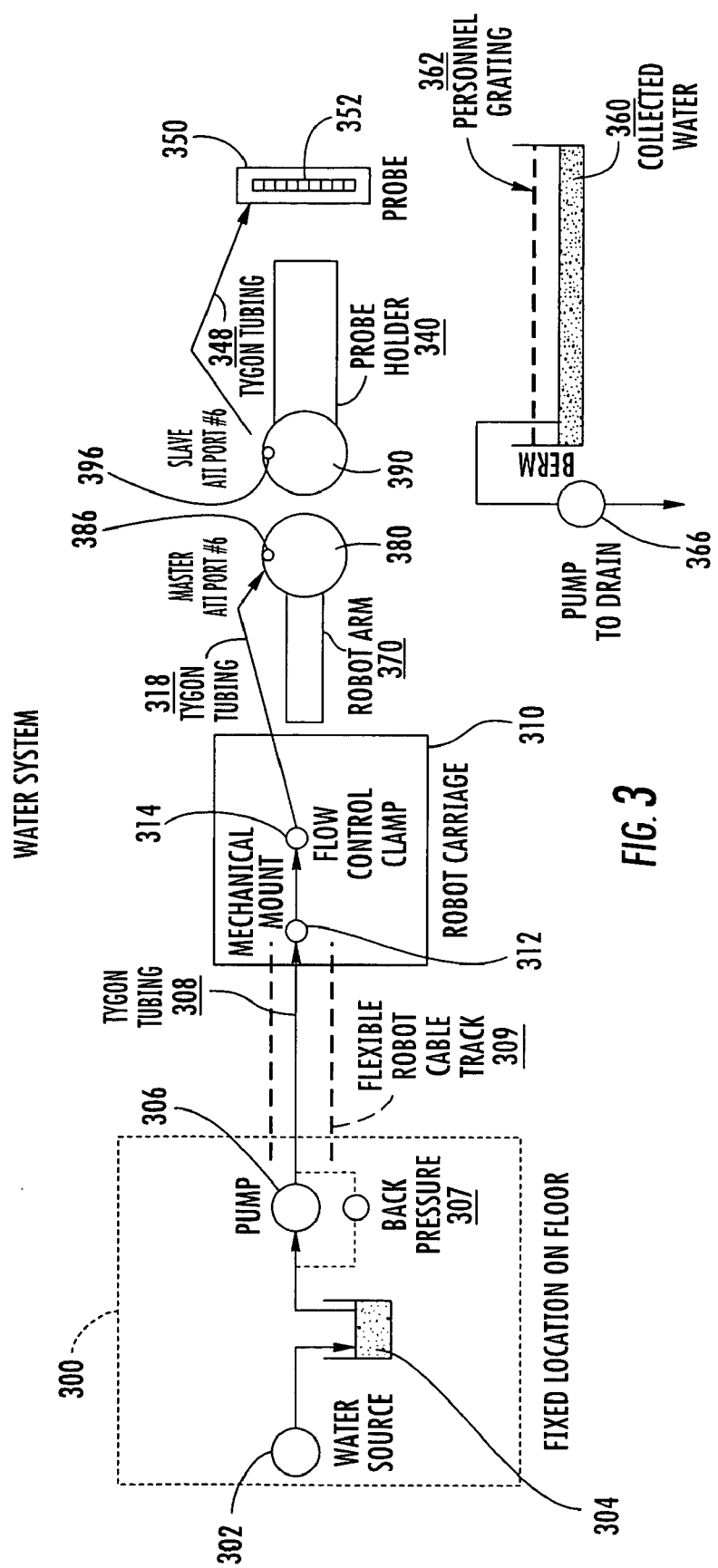
FIG. 3 is a schematic diagram of an embodiment of a water system for an ultrasonic inspection system of the present invention.

FIG. 3 is a schematic diagram of an embodiment of a water system for an ultrasonic inspection system of the present invention. Water, or another fluid, may be used as a couplant for ultrasonic transducers 352 of the inspection probe 350. To provide water for coupling the ultrasonic transducers 352, a water source 302 may provide water into a reservoir 304 from which water is extracted by a pump 306, possibly including a back pressure valve 307. Tubing 308, such as Tygon® tubing of St. Gobain Performance Plastics Corporation of Worcester, Mass., may be attached between the pump 306 and the motion control system, such as between the pump 306 and a mechanical mounting 312 on the robot carriage 310. The tubing 308 between the pump 306 may be carried through a flexible robot cable track 309 to the robot carriage 310. The robot carriage 310 may include a flow control clamp 314 to turn on and off the flow of water from the robot carriage 310. The water may continue from the flow control clamp 314 through additional tubing 318 to a port 386, referred to as ATI port number 6, on the end of the robot arm 370. A robot interface 380 may be included at the end of the robot arm 370 for providing a master-slave attachment between the robot arm 370 and a device attached to the end of the robot arm 370. For example, a probe extension coupler 340 may include a corresponding ATI interface 390 which operates to connect the extension coupler 340 to the robot arm 370, and specifically to connect the various feeds from the robot arm 370 ATI interface 380 to the extension coupler 340 ATI interface 390. Additional tubing 348 passes the water from the extension coupler 340 to the ultrasonic transducers 352 of the inspection probe 350. During inspection, the water being used as a couplant may be passed between the ultrasonic transducers 352 and the surface of the structure under inspection. Water that falls from the structure under inspection to the floor may be collected and recycled through the water system. For example, the excess water from the structure may pass through a grating 362 into a reservoir 360 from which a pump 366 will return the water to the original reservoir 304.

Figure 4:
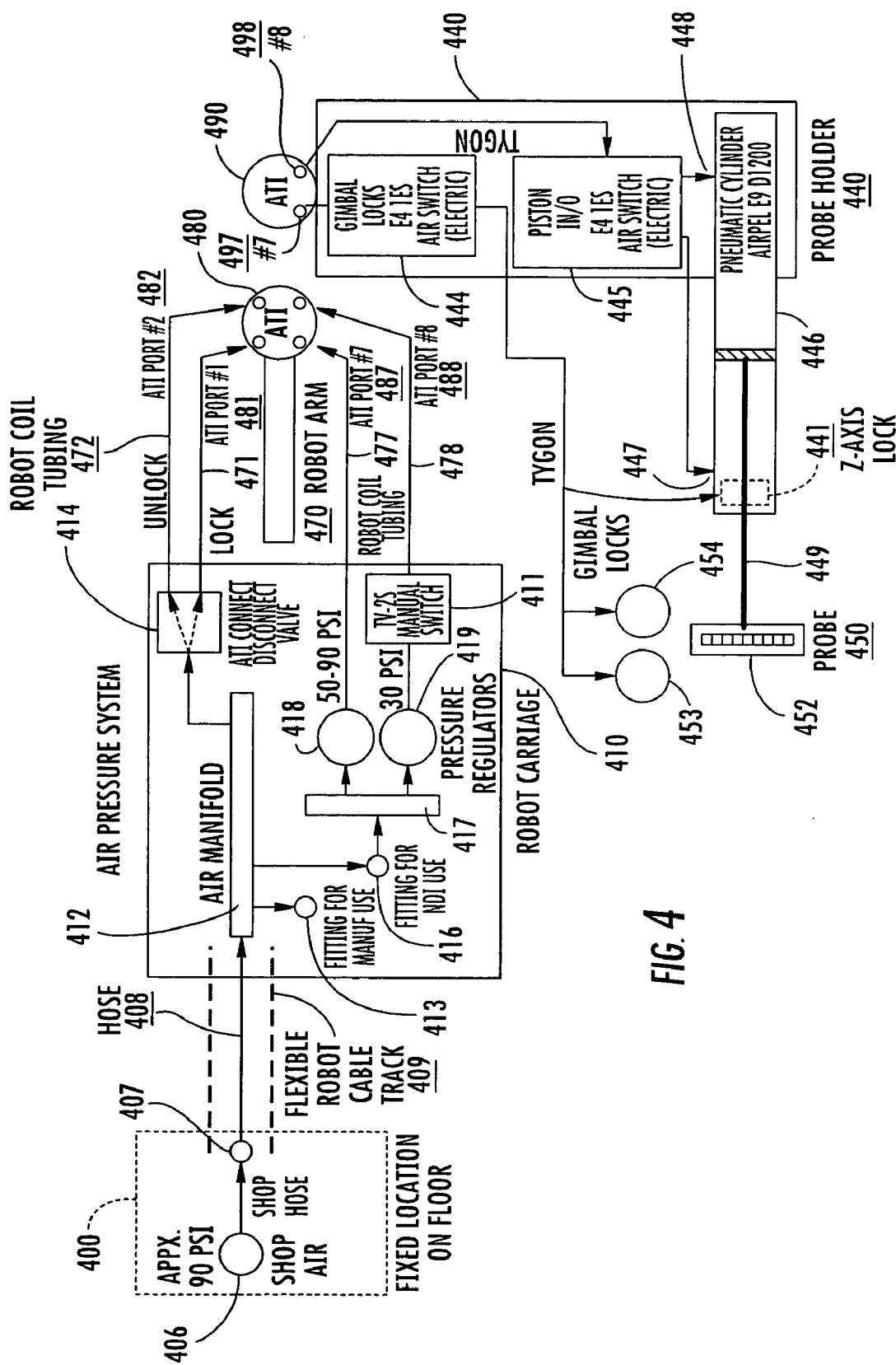
FIG. 4 is a schematic diagram of an embodiment of a pneumatic system for an ultrasonic inspection system of the present invention.

FIG. 4 is a schematic diagram of an embodiment of a pneumatic system for an ultrasonic inspection system of the present invention. Many components of an ultrasonic inspection system may rely upon air pressure for operation. For example, a dual-action pneumatic cylinder 446 of an extension coupler 440 may use air pressure to extend and retract an inspection probe 450. Similarly, the inspection probe 450 may use air pressure for activation of pneumatic cylinders of an axial braking system to lock sled appendages in fixed positions for traveling over a hole or off an edge of a structure. A pneumatic air pressure system according to the present invention may use an air supply 406, such as an air compressor providing approximately 90 psi (pound per square inch) pressure. The hose from the air supply 406 may be attached to a fitting 407 to which a hose 408 may be connected for running through the flexible robot cable track 409. The hose 408 may attach to an air manifold 412 of a robot carriage 410. The air manifold 412 may feed a fitting 413 for manifold use, an ATI connect/disconnect valve 414, and a fitting 416 for use by the extension coupler 440 and inspection probe 450 for nondestructive inspection. A second air manifold 417 may supply air to pressure regulators 418, 419 to control the pressure provided to various components of the ultrasonic inspection system. For example, a pressure regulator 418 may provide between 50 to 90 psi pressure through a tube 477 connected to ATI port number 7 487 which supplies ATI interface 490 port 7 497 that feeds the brake cylinders 453, 454, also referred to as gimbal locks, of a braking system on the inspection probe 450 and a z-axis lock 441 on the extension coupler 440. The z-axis lock 441 is included as part of the extension coupler 440 to prevent the extension coupler from pressing the inspection probe 450 through a hole or off an edge of the part. Rather, the z-axis lock is activated to hold the inspection probe 450 at a fixed location corresponding to the position of the surface of the structure proximate a hole or edge. When the inspection probe 450 has cleared the hole and returns over the structure, the z-axis lock 441 is released to permit the extension coupler 440 to continue to press the probe 450 against the structure. A pressure regulator 419 may provide approximately 30 psi pressure through a tube 478 to ATI port 8 488 which feeds ATI interface 490 port 8 498 that supplies air pressure to the pneumatic cylinder 446 of the extension coupler 440.

A manual switch 411 may be included in the ultrasonic inspection system for controlling pressure to the pneumatic cylinder 446 of the extension coupler 440 to control whether the pneumatic cylinder 446 is activated to extend the inspection probe 450 against a structure. For example, during set-up operations it may be advantageous to have the pneumatic cylinder 446 retracted rather than extended in order to provide separation between the structure and the inspection probe. However, in order to operate the ultrasonic inspection system for nondestructive inspection of the structure, the manual switch 411 may be turned on or opened to provide air pressure to the pneumatic cylinder 446 in order to extend the probe 450 against the structure. Electrical switches 444, 445 may be included, such as in the inspection coupler 440, to control the flow of air and activation of the pneumatic cylinders 446, 453, 454, 441 of the extension coupler 440 and inspection probe 450. The electrical air switch 444 that controls activation of the brake cylinders 453, 454 and z-axis lock 441 may be either opened or closed to control whether pressure is provided to those pneumatic cylinders 453, 454, 441. The electronic air switch 445 for the dual-action pneumatic cylinder 446 of the extension coupler 440 may be capable of providing air pressure to two valves 447, 448 on the pneumatic cylinder 446 in order to extend and retract the piston rod of the dual-action pneumatic cylinder 446.

Figure 5:
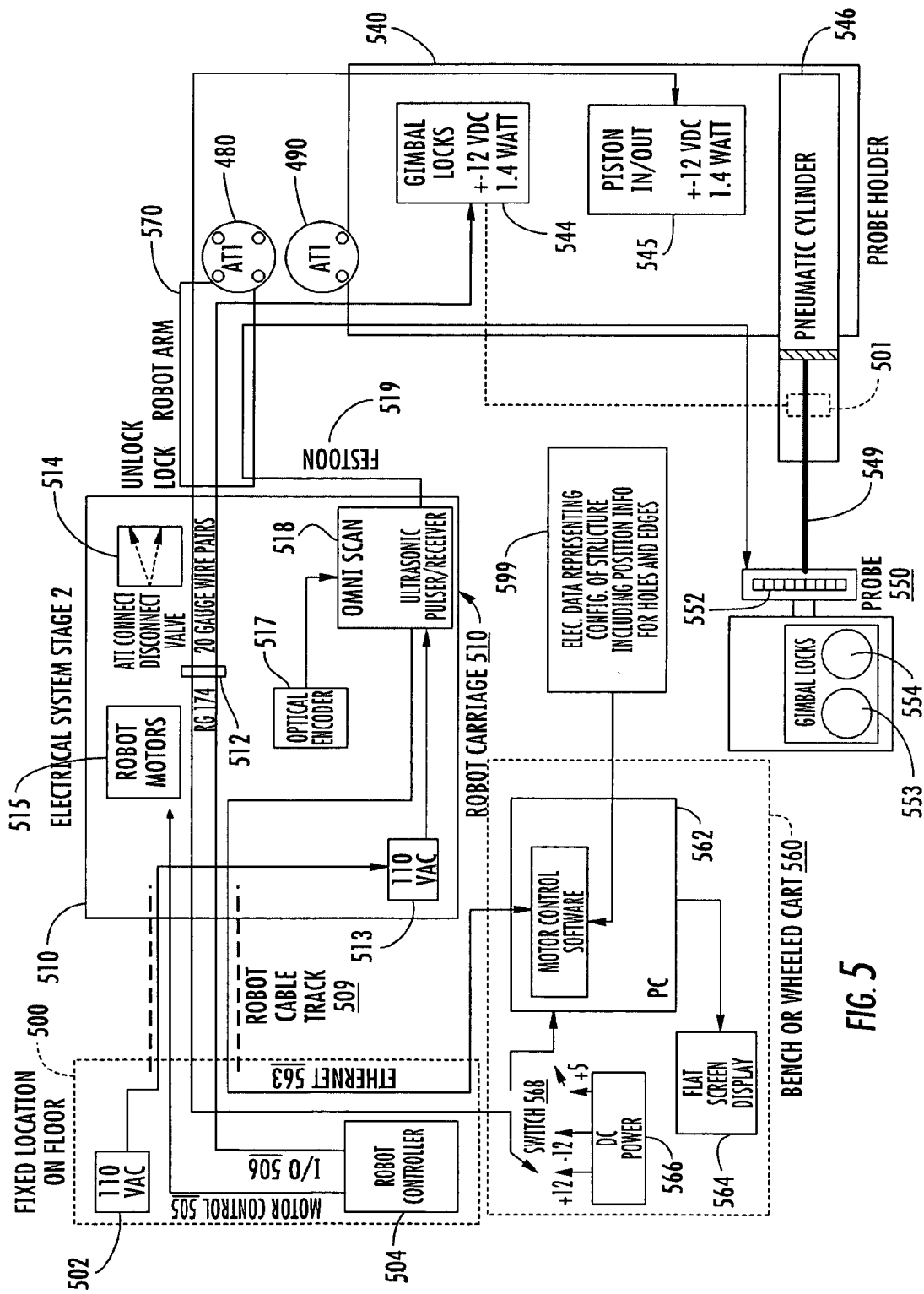
FIG. 5 is a schematic diagram of an embodiment of an electrical control system for an ultrasonic inspection system of the present invention.

FIG. 5 is a schematic diagram of an embodiment of an electrical control system for an ultrasonic inspection system of the present invention. The electrical control system may include power sources, motion control subsystems, and inspection data subsystems. For example, the electrical control system of FIG. 5 includes a DC power source 566 which may be located on a fixed bench location or on a wheeled cart used for nondestructive inspection, a 110 volt AC power source 502 which may be located at a fixed location, and an intermediate 110 volt AC power source 513 which may be positioned to ride on the robot carriage 510. A robot controller 504 may be included in the electrical control system to operate the motion control of a robot carriage 510, rail system, and robotic arm 570 and to operate pneumatic cylinder locks 553, 554, 501 on an inspection probe 550 and an extension coupler 540. An inspection data subsystem may include a computer 562 such as a personal computer with a display unit 564 in communication with an ultrasonic inspection device, such as an OmniScan™ ultrasonic pulser/receiver unit 518 from RID Tech of Quebec, Canada, in communication with ultrasonic transducers 552 of the inspection probe 550. An optical encoder 517 may also be included for transmitting position data related to the location of the inspection probe on the structure under inspection. For example, an optical encoder may measure the position of the robot carriage 510 along the rail system and provide position data to either the ultrasonic inspection device 518 or the computer 562.

The operation of the electrical control system may include selectively extending or retracting the pneumatic cylinder 546 of the extension coupler 540 by activating or deactivating a switch 568 for a power source 566. Separately, the robot controller 504 may control the robot carriage 510, robot arm 570, and inspection probe 550. For example, the 110 volt alternating current power source 502 may provide power to an intermediate 110 volt alternating current source 513 of the robot carriage 510 which supplies power to the ultrasonic inspection device 518 thereby providing power for the optical encoder 517 and the inspection probe 550. Similarly, the robot controller 504 may provide sufficient power for activating electronic switches 544 in the extension coupler 540 for controlling air pressure to brake cylinders 553, 554 in the braking system of the inspection probe 550 and z-axis lock 501 for the pneumatic cylinder 546 of the extension coupler 540. Motor control signals 505, also referred to as robotic motion control signals, may be provided from the robot controller 504 to the robot motors 515 to drive the robot carriage 510 and the robot arm 570.

The input/output signals 506 from the robot controller to the electronic air switches 544 complement the motor control signals 505 for the robot carriage 510 and the robot arm 570. Specifically, the input/output signals 506, in coordination with the activation of the pneumatic cylinder 546 of the extension coupler 540, permit the robot controller 504 to move the robot carriage 510 and robot arm 570 for inspection of a structure without requiring the cost and complexity associated with programming the motion control system for the specific contours of the structure. Accordingly, an embodiment of the present invention reduces the accuracy requirements of a robot controller 504 and, thereby, reduces the robot hardware and software costs and cost of technicians operating and programming the robot software. To reduce the accuracy requirements of the robot controller 504, the combination of an extension coupler 540 and inspection probe 550 creates a nondestructive inspection apparatus capable of inspecting over holes and off edges of the structure. More particularly, the extension coupler 540 compensates for surface contours not programmed into the robot controller by exerting an outward force to press the probe 550 against the structure at all times regardless of the particular contour of the surface of the structure. For example, the robot controller 504 need only adjust the robot arm 570 sufficient to position the inspection probe 550 within approximately six inches of the surface of the structure. The extension coupler 540 compensates for the additional six inch distance, and may compensate for as much as twelve inches in the z-axis, by extending the piston rod 549 from the pneumatic cylinder 546 of the extension coupler. The length of compensation in the z-axis by an embodiment of an extension coupler according to the present invention is limited by the length of extraction and retraction of a piston rod of a dual action cylinder and the corresponding structure supporting the travel of the piston of the dual action cylinder; larger cylinders may compensate for more than twelve inches of z-axis travel.

The inspection probe 550 compensates for x- and y-axes variations in the contour of the surface of the structure using rotatably attached part-riding structures of the inspection probe 550. For example, the inspection probe 550 may include a pair of sled appendages attached to a frame of the inspection probe which are rotatably attached in one axis and have a frame rotatably attached or hinged about a perpendicular axis to provide freedom of motion about two axes such as an x- and y- pair of axes. An ultrasonic inspection system according to the present invention is capable of scanning over holes and off edges of the part by locking the rotating motion of the inspection probe part-riding structures and outward force of the pneumatic cylinder 546 of the extension coupler 540. For example, as the robot controller 504 moves the inspection probe 550 over a hole, the robot controller 504 may activate piston locks 553, 554, 501 on the inspection probe 550 and extension coupler 540 to fix the position of the rotatable structures of the inspection probe 550 and piston rod 549 of the pneumatic cylinder 546 of the extension coupler 540 for traveling over the hole and release the piston locks 553, 554, 501 when the robot controller 504 positions the inspection probe 550 past the hole to continue scanning the structure by way of the part-riding functionality of the inspection probe 550. In general terms, control software, such as part of the robot controller 504, informs the braking system of the inspection probe when a hole in the structure starts, i.e., when to lock the positions of sled appendages of the inspection probe 550, and when the hole in the structure ends, i.e., when to unlock sled appendages to resume following the surface contour and shape of the structure. Control software may similarly inform the braking system of the extension coupler 540 when the inspection probe 550 is about to travel over a hole so the extension coupler 540 does not attempt to press the probe 550 through the hole, i.e., when to lock the z-axis position of the piston rod 549, or similar extending and retracting rod, of the extension coupler 540, and when the probe has passed over the hole, i.e., when to unlock the z-axis to resume pressing the inspection probe 550 against the surface of the structure.

As the non-destructive inspection of a structure occurs using an embodiment of the present invention, an ultrasonic inspection device 518 receives inspection data from ultrasonic transducers 552 of an inspection probe 550. The ultrasonic inspection device 518 provides the inspection data, possibly associated with position information from an optical encoder 517, to a computer 562 for evaluation by a technician on a display screen 564. Although an ultrasonic device 518 may provide visual recognition of the inspection, a separate computer 562 using specialized inspection display software may provide customized information for the benefit of the technician. For example, the inspection data software may combine the inspection data from ultrasonic transducers 552 with position data from an optical encoder 517 with electronic data 599 representing the configuration of the structure under inspection, including position information for holes and edges of the structure, to provide the technician a virtual image of the ongoing non-destructive inspection by the ultrasonic inspection system.

An extension coupler according to the present invention provides a connection between a motion control system, such as connecting a pedestal robot mounted onto a rail system, and an inspection probe. An extension coupler accommodates for depth changes between the position of a motion control system and the surface of a structure to allow an inspection probe to scan the structure regardless of changing curved surfaces. By pressing the inspection probe against the structure, an extension coupler prevents the motion control system from needing to adjust for surface contours of a structure. To adjust for surface contours by pressing the inspection probe against the structure, an extension coupler may use a double action cylinder, typically a double action pneumatic cylinder, to maintain constant pressure of the inspection probe against the structure. For example, as the inspection probe moves the surface of a structure, the extension coupler will extend and retract to maintain a consistent pressure on the inspection probe for contacting the structure.

Figure 6:
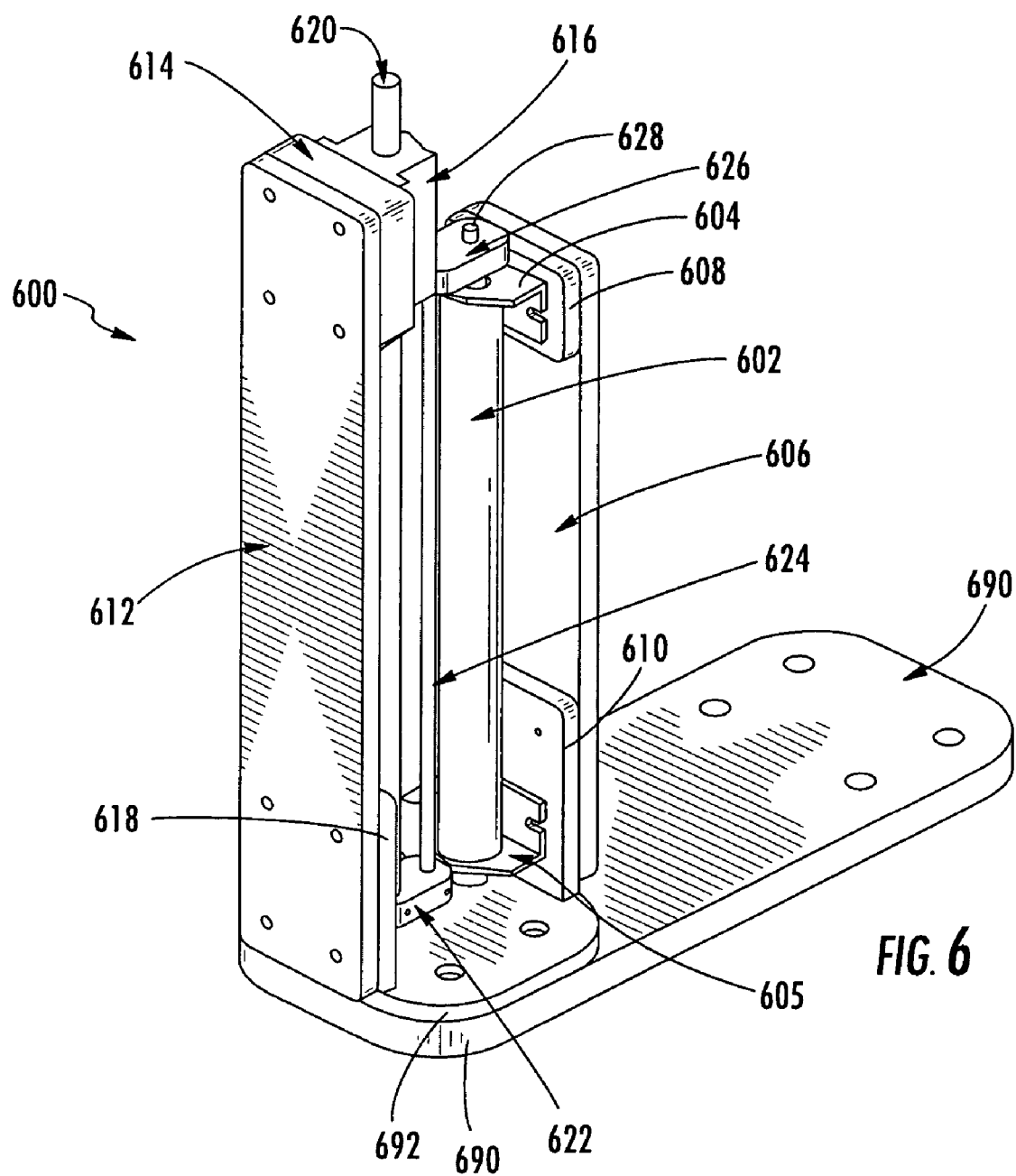
FIG. 6 is a schematic diagram of an embodiment of a probe extension coupler of the present invention.
Figure 7A:
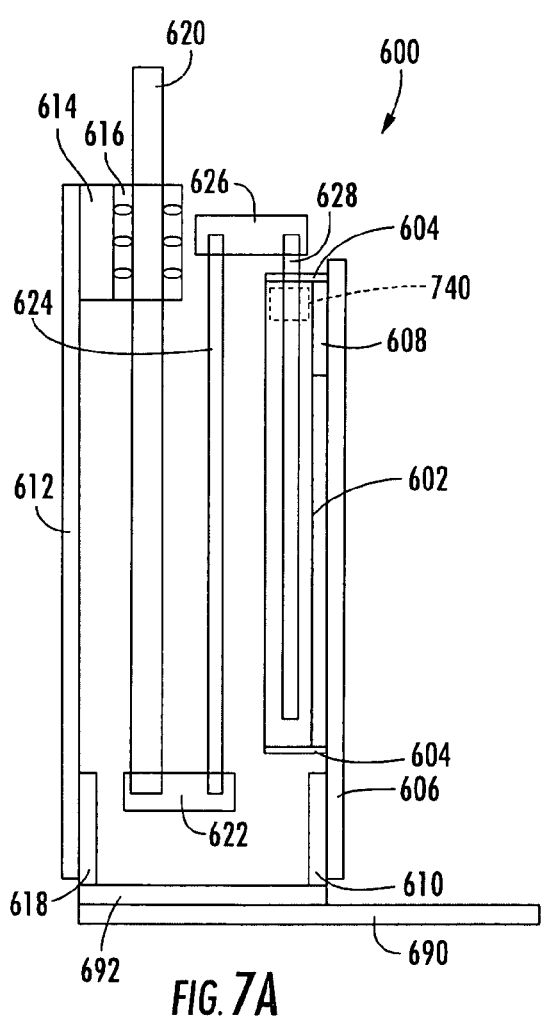
FIG. 7A is a schematic diagram of an embodiment of a probe extension coupler of the present invention in a retracted position.
Figure 7B:
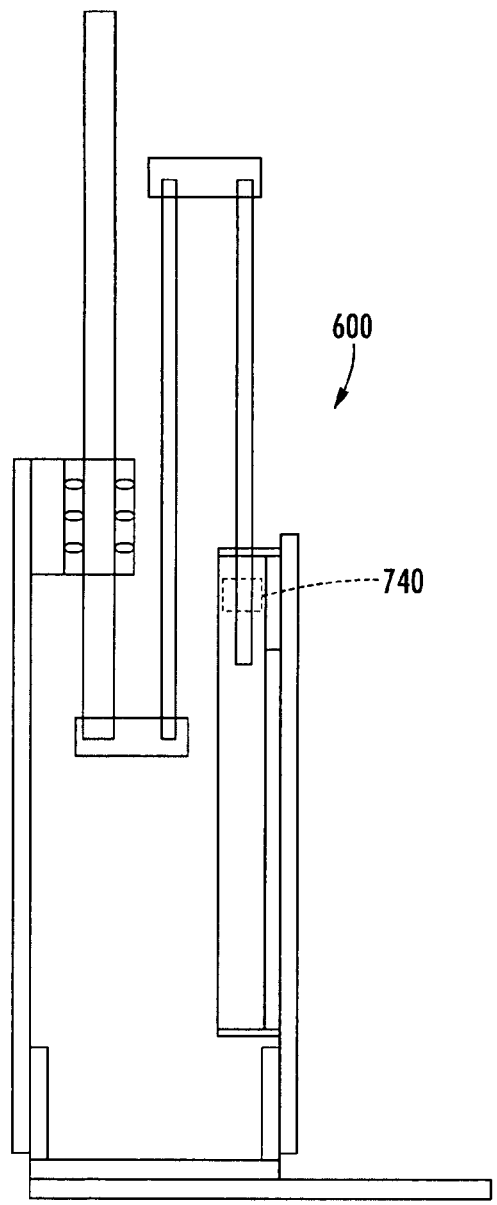
FIG. 7B is a schematic diagram of the extension coupler of FIG. 7A in an extended position.

FIGS. 6, 7A, and 7B are schematic diagrams for an embodiment of an extension coupler of the present invention. The extension coupler 400 includes a support structure to house a double action cylinder 602 with an extending and retracting cylinder rod 628. A double action cylinder 602 pushes out in one direction, extends or extracts, and pulls in another direction, retracts. An extension coupler 600 may include a support structure that includes a main base plate 692 for mounting the extension coupler 600 to a motion control system, such as to the end of a robot arm. A pair of vertical plates 612, 606 may be mounted on opposing sides of the main base plate 692. The double action cylinder 602 may be mounted to one of the vertical plates 606, also referred to as the cylinder holder vertical plate, which may be accomplished using a pair of cylinder brackets 604, 605 at either end of the double action cylinder 602. One cylinder bracket 605 may be mounted to the cylinder holder vertical plate 606 by attachment to a u-bracket section 610 mounted to the main base plate 692 and to which the cylinder holder vertical plate 606 is attached. The other cylinder bracket 604 may be mounted to a spacer section 608 attached to the cylinder holder vertical plate 606. The main base plate 692 and two opposing u-bracket sections 610, 618 may be attached to form a u-bracket for supporting an end of the extension coupler 600. The vertical plates 612, 606 may be mounted to the main base plate 692 by attachment to the opposing u-bracket sections 618, 610.

A pillow block bearing 616 may be mounted to the vertical plate 612, also referred to as the shaft holder vertical plate, which may be accomplished by using a pillow block bearing mount 614. The pillow block bearing 616 supports rotation and translation of a transducer extension rod 620, also referred to as a main drive shaft. The transducer extension rod 620 is connected to an inspection probe. Although a pillow block bearing might be used to support extension of the cylinder rod 628, also referred to as a piston rod, the pillow block bearing 616 of the depicted extension coupler 600 supports the transducer extension rod 620 which is connected to a transition rod 624, also referred to as a push rod, by an interface plate 622, also referred to as a lower rod interface plate. The transition rod 624 is connected to the cylinder rod 628 by an interface plate 626, also referred to as an upper rod interface plate. When the cylinder rod 628 extends, the transition rod 624 transfers the extending motion to the transducer extension rod 620. When the cylinder rod 628 retracts, the transition rod 624 transfers the retracting motion to the transducer extension rod 620. An advantage of using such a configuration is that the extension coupler 600 can use different dimensions of rods, such as 0.25 inch diameter cylinder and transition rods 628, 624 and a 0.625 inch diameter transducer extension rod 620. Another advantage for this configuration using a transition rod 624 and interface plates 622, 626 between the transducer extension rod 620 and cylinder rod 628 is to provide stability for the transducer extension rod 620 rather than exerting sheer pressure on a thin cylinder rod 628 which might break a glass cylinder in the dual action cylinder 602. If necessary, or as desired, an extension base plate 690, also referred to as an ATI interface, may be mounted to the main base plate 692 to provide quick connect and disconnects for supply lines, such as a pneumatic air pressure supply line, a water couplant supply line, electrical supply lines, and data input output lines, to an ATI interface of a robot arm of a motion control system.

The dual action cylinder 602 operates using regulated air to provide the dual action of extension and retraction and to exert a consistent pressure, typically set between fifty to seventy psi pressure, on the inspection probe to press the inspection probe against the surface of the structure for inspection with two to three pounds of force. For example, if the extension coupler is configured to exert a continuous pressure of fifty psi to the inspection probe against the structure, as the inspection probe moves over a portion of the structure where the surface of the structure is contoured to decrease the distance between the structure and the robot, the extension coupler will sense an increased pressure and compensate for the surface contour by decreasing the outward force on the inspection probe until the extension coupler retracts to maintain the continuous two pounds force on the inspection probe against the structure. A flow control valve may be used to provide a full range of air flow to the pneumatic cylinder to provide the proper speed of actuation and retraction of pressure exerted to the inspection probe to compensate for surface contours of the structure.

In FIGS. 7A and 7B, a z-axis lock 740, also referred to as a z-axis brake or z-brake, may be included in the dual action cylinder 702, or just above the dual action cylinder 702, to lock the position of the cylinder rod 628. When an inspection probe travels over a hole or off an edge of the structure during inspection, the dual action cylinder 602 should not press the inspection probe through the hole or over the edge of the structure, but should remain in the current extended or retracted position so the inspection probe will return to the surface of the structure when the inspection probe clears the hole or returns from off the edge of the structure. One way to accomplish holding the extended or retracted position of the dual action cylinder 602 is to have a z-axis lock 740, such as an inflatable bladder, exert pressure on the cylinder rod 628 to prevent the cylinder rod from extending to push the inspection probe through a hole or over an edge of the structure.

Inspection probes according to the present invention are described fully in U.S. Pat. No. 7,337,673. Basic functionality and structure of an embodiment for an inspection probe according to the present invention are described below with reference to FIGS. 8 and 9.

Conventional part-riding probes, probes which contact and ride along the surface of the structure under inspection, may fall through a large hole or off the side of a part rather than having the ability to travel over holes and off the edge of a part for inspection. Using conventional part-riding probes, a structure typically is scanned in a manner to go around holes and to not inspect near edges, leaving the edges of the structure to be inspected by a second inspection method, such as by a technician using a manual pulse echo scanning device.

By comparison, a part-riding inspection probe according to the present invention permits inspection over holes and off edges of a structure. Sled appendages, or sleds, of a probe according to the present invention are linear extensions rotatably attached to the bottom of the probe and upon which the probe rides over a surface of the structure. An axial braking system according to the present invention operates to temporarily fix the current positions of the sled appendages to maintain those positions while the probe travels over a hole or off an edge of the structure. An axial braking system may operate in one or more axes. For example, the braking system may lock simply in an x-axis, in both x- and y-axes, or in x-, y-, and z-axes; although, as described above, fixing an inspection probe in the z-axis may be accomplished using a z-axis lock on an extension coupler. The axial braking system fixes the position of the sled appendages by locking the axes of motion of the sled appendages before traveling over a hole or off an edge of the structure.

Figure 8:
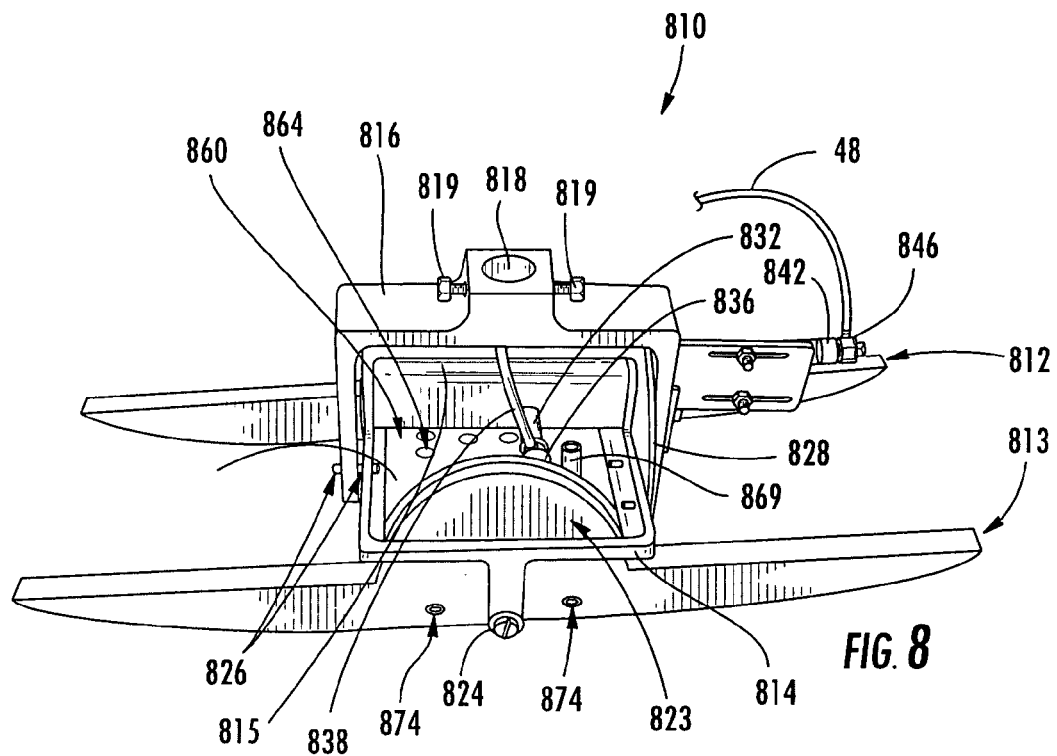
FIG. 8 is a diagram of an embodiment of an inspection probe according to the present invention.
Figure 9:
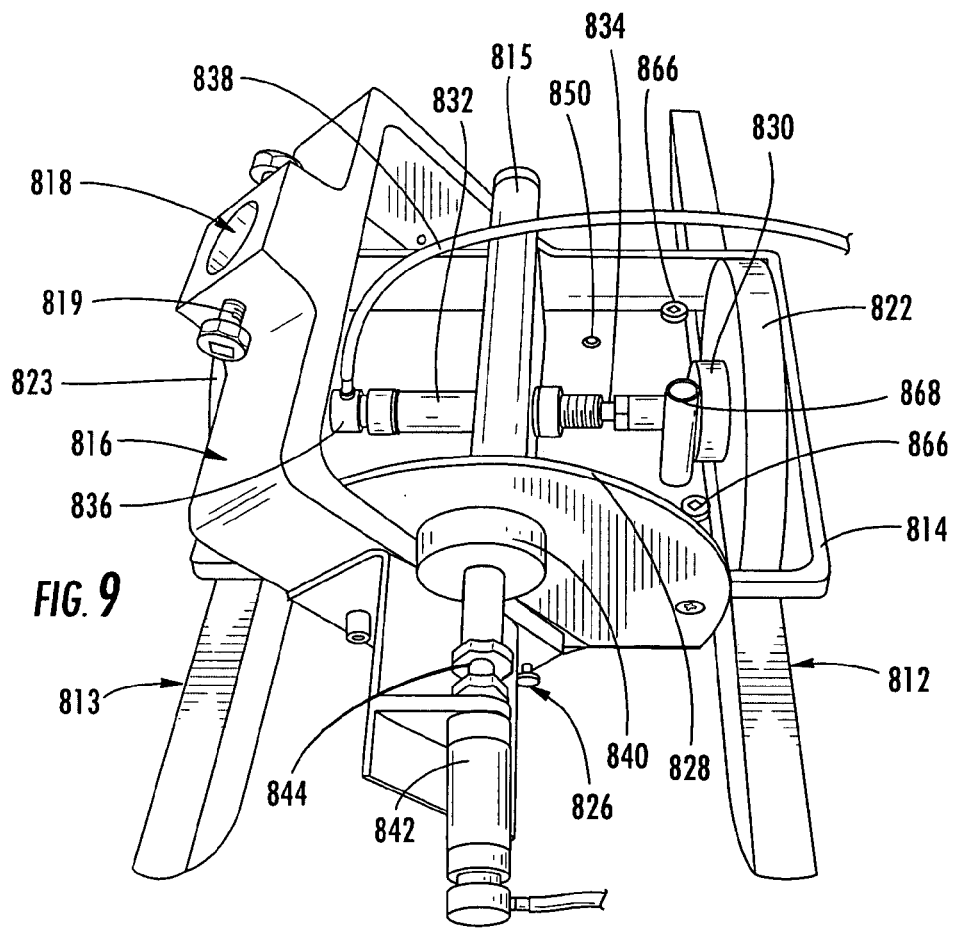
FIG. 9 is another view of the diagram of the probe of FIG. 8.

FIGS. 8 and 9 are schematic diagrams of an embodiment of an inspection probe according to the present invention, also generally referred to as a probe and as a part-riding inspection probe. The inspection probe 810 includes two sled appendages 812, 813 located on opposite sides of the inspection probe 810. The sled appendages 812, 813 are rotatably attached to a frame member 814 of the inspection probe 810 about a first axis 824 defining a first direction of motion for the sled appendages 812, 813, also referred to as an x-axis, front-to-back tilt axis, or pitch axis. The frame of the inspection probe 810 also includes a second frame member 816 which is rotatably connected to the first frame member 814 about a second axis 826 defining a second direction of motion for the sled appendages 812, 813, also referred to as a y-axis, side-to-side slant axis, or roll axis. By having two rotational axes, the sled appendages 812, 813 are capable of rotating in at least two directions of motion with respect to a motion control system connected to the inspection probe 810, such as by way of an attachment at the opening 818 and securing screws 819 to connect to a transducer extension rod of an extension coupler, to compensate for surface variations of the structure, such as shape and contour characteristics of the surface for which the motion control system does not adjust. Further, because as described below, a transducer holder or bubbler shoe for an inspection apparatus of the present invention is connected to sled appendages, rather than the frame, the transducers maintain the same position and orientation as achieved by the sled appendages, thereby providing the transducers a consistent orientation with respect to the surface of the structure over which the inspection apparatus rides on the sled appendages. Maintaining a consistent orientation, distance and angle, of the transducers with respect to the surface of the structure ensures consistent quality of inspection by the transducers.

At least one of the sled appendages 812, 813 includes an upper portion 822, 823 that functions as a stationary brake plate against which a brake disc 830 of the axial braking system can be applied to fix the position of the sled appendage about the first axis of motion 824. An axial braking system of an embodiment of the present invention may also include a pneumatic brake cylinder 832 with an extendable piston arm 834 to which a brake disc 830 is attached at the distal end of the extendable piston arm 834 protruding from the brake cylinder 832. A brake cylinder 832 may be activated by any conventional method, such as by compressing a fluid, typically air, through a supply line 838 into a valve 836 attached to the brake cylinder 832. When the brake mechanism is activated, the compression of fluid causes a piston inside the brake cylinder 832 and attached to the distal end of the extendable piston arm 834 inside the brake cylinder 832 to force the extendable piston arm 834 out of the brake cylinder 832 to force the brake disc 830 to press against the stationary brake plate 822, 823 of one or more sled appendages 812, 813.

To fix the position of the sled appendages in the second axis of motion 826, a second brake plate 828 may be affixed to the first frame member 814 to permit a second brake mechanism 840, 842, 844, 846, 848, to engage the second stationary brake plate 828 in the same manner that the first brake mechanism 830, 832, 834, 836, 838 engages the first stationary brake plate 822, 823 to fix the position of the sled appendages 812, 813 about the first axis of motion 824. The first frame member 814 may include a vertical support member 815 connected to the second stationary brake plate 828 to provide stability between the first frame member 814 and the second stationary brake plate 828, such as when a brake disc 840 is pressed against the second stationary brake plate 828 to fix the position of the sled appendages in the second axis of motion 826. An axial braking system of an alternative embodiment may also include a brake mechanism in a third direction of motion, such as a vertical z-axis with respect to the surface of the structure, and may be incorporated into an attachment to a motion control system, such as an extension coupler.

The inspection probe 810 includes at least one pulse echo ultrasonic transducer 850. If not using a couplant between the transducers 850 of the inspection probe 810 and the structure, a transducer holder may be attached to the sled appendages 812, 813 to support the transducers 850, such as supported in an array where a plurality of transducers are used to increase the inspection coverage area. As mentioned above, by attaching the transducer holder, or bubbler shoe as described below, to the sled appendages 812, 813 the transducer holder and transducers 850 supported thereby also maintain constant orientation with the surface of the structure over which the inspection probe 810 rides because the inspection probe 810 rides over the surface of the structure on the sled appendages 812, 813. Because inspection of a structure typically requires ensuring that the transducers maintain constant orientation, distance and angle, with respect to the surface of the structure, attaching a transducer holder, or bubbler shoe, to sled appendages ensures that the transducer holder, or bubbler shoe, and transducers supported thereby also maintain constant orientation with respect to the surface of the structure for consistent quality of inspection by the transducers.

If a couplant is to be used to couple the ultrasonic signals from the transducers 850 into the structure and reflected from the structure back to the transducers 850, a bubbler shoe 860 may be incorporated into the inspection probe 810. The bubbler shoe 860 individually couples each transducer 850 rather than using a single cavity to couple all of the transducers 850. A bubbler shoe may include a top layer 862 that includes holes 864 to permit access to the transducers 850, such as by the transducer protruding through the holes 864 in the top layer 862 or by permitting a wired connection through the holes 864 in the top layer 862 for communication with the transducers 850. The top layer 862 may also include one or more fluid inlets 868, 869 through which a couplant may be injected into the bubbler shoe 860. The bubbler shoe 860 may also include a bottom layer that, together with the top layer 862, define a cavity through which a couplant from the fluid inlet 868, 869 can flow to individually couple each transducer 850. By way of example, such cavities may be a single open cavity providing a fluid path to each transducer or may be a cavity structured with a manifold configuration whereby the couplant passes into separate subcavities that lead to the individual transducers. The bottom layer includes holes through which the couplant passes to couple the transmission of ultrasonic signals from the transducers 850. The transducers 850 may pass through the holes in the bottom layer, may terminate inside the cavity, or may terminate within the bottom layer.

The invention should not be limited to the specific disclosed embodiments. Specific terms are used in a generic and descriptive sense only and not for purposes of limitation.

That which is claimed:

1. A system for non-destructive inspection of a structure, comprising:
   a motion control system comprising a robot control system, wherein the robot control system comprises a robotic arm;
   an extension coupler attached to the robotic arm, the extension coupler having an extendable and retractable distal end; and
   an inspection probe attached to the distal end of the extension coupler, configured for traveling over holes and off edges of the structure, and comprising at least one pulse echo ultrasonic transducer configured for inspecting the structure as the inspection probe and transducer are moved over the structure by at least one of the motion control system and extension coupler, wherein the extension coupler is configured to extend and retract the first end to which the inspection probe is attached for applying pressure to the inspection probe to press the inspection probe against the structure, and wherein the extension coupler is configured to temporarily lock the extended or retracted position of the inspection probe with respect to the extension coupler when the inspection probe passes over one or more of the edge of the hole, over the hole, over the edge of the structure, and past the edge of the structure, thereby preventing the inspection probe from extending past the surface of the structure into the hole or off the edge of the structure by the pressure applied to the inspection probe by the extension coupler.

2. The system of claim 1, wherein the robot control system is configured for being attached to and moved along a rail system, and wherein the motion control system further comprises a rail system to which the robot control system is attached, the rail system being capable of moving the attached robot control system.

3. The system of claim 2, wherein the motion control system comprises a controller for controlling the movement of at least one of the rail system and the robot control system.

4. The system of claim 2, wherein the rail system is configured for controlling linear motion to the attached motion control system.

5. The system of claim 2, wherein the rail system comprises:
   a rail support structure; and
   a robot carriage to which the robot control system is mounted and for traveling along the rail support structure, thereby moving the robot control system along the rail system.

6. The system of claim 1, wherein the motion control system comprises an optical encoder capable of measuring and transmitting the position of the motion control system with respect to the structure.

7. The system of claim 1, wherein the robot control system comprises a pedestal robot configured for controlling the motion of the extension coupler in at least two directions of motion.

8. The system of claim 1, wherein the extension coupler comprises:
   a dual action cylinder having an extendable and retractable cylinder piston rod having a first end protruding from the dual action cylinder;
   a transition rod connected to the protruding first end of the cylinder piston rod for translating the motion of the cylinder piston rod, the transition rod having a first end connected to the protruding distal end of the cylinder piston rod and a second end; and
   a transducer extension rod connected to the second end of the transition rod for translating the motion of the transition rod and the cylinder piston rod, the transducer extension rod having a first end connected to the second end of the transition rod and a second end forming the distal end of the extension coupler.

9. The system of claim 8, wherein the extension coupler further comprises a pillow block bearing surrounding a portion of the transducer extension rod between the first and second ends of the transducer extension rod and configured for stabilizing the transducer extension rod.

10. The system of claim 1, wherein the inspection probe comprises:
    a frame configured for attaching to the second end of the extension coupler and for supporting the transducer;
    at least one sled appendage configured for supporting the frame while traveling over a surface of the structure and rotatably connected to the frame; and
    a braking system capable of affixing the respective positions of the frame and sled appendage in
    at least a first direction of motion about a first axis defined by the rotatable connection of the frame and the sled appendage.

11. The system of claim 10, wherein the motion control system is capable of providing a braking signal to the braking system of the probe based upon a determination of the location of the probe with respect to a predetermined location of at least one of a hole and an edge of the structure known to the motion control system.

12. The system of claim 1, wherein the inspection probe comprises:
    a bubbler shoe configured for supporting a plurality of transducers and dispersing a couplant between the transducers supported thereby and the surface over which the inspection probe travels; and
    a plurality of transducers supported by the bubbler shoe.

13. The system of claim 1, wherein the motion control system is configured for interpreting electronic data representing the configuration of the structure for controlling movement of the probe over the structure for inspection and for providing the ability to communicate the location of holes and edges to at least one of the extension coupler and the inspection probe.

14. A system for non-destructive inspection of a surface of a structure, wherein the surface comprises at least one edge defined by at least one of a hole cut-out in the surface and an extent of the surface, comprising:
    a motion control system comprising a robot control system, wherein the robot control system comprises a robotic arm;
    an extension coupler attached to the robotic arm, the extension coupler having an extendable and retractable distal end; and
    an inspection probe attached to the distal end of the extension coupler and comprising at least one pulse echo ultrasonic transducer configured for inspecting the structure as the inspection probe and transducer are moved over the structure by at least one of the motion control system and extension coupler, wherein the inspection probe is configured for traveling past the at least one edge and off the surface of the structure and returning onto the surface of the structure,
    wherein the extension coupler is configured to extend and retract the first end to which the inspection probe is attached for applying pressure to the inspection probe to press the inspection probe against the surface of the structure.

15. The system of claim 14, wherein the extension coupler comprises:
    a dual action cylinder having an extendable and retractable cylinder piston rod having a first end protruding from the dual action cylinder;
    a transition rod connected to the protruding first end of the cylinder piston rod for translating the motion of the cylinder piston rod, the transition rod having a first end connected to the protruding distal end of the cylinder piston rod and a second end; and a transducer extension rod connected to the second end of the transition rod for translating the motion of the transition rod and the cylinder piston rod, the transducer extension rod having a first end connected to the second end of the transition rod and a second end forming the distal end of the extension coupler.

16. The system of claim 15, wherein the extension coupler further comprises a pillow block bearing surrounding a portion of the transducer extension rod between the first and second ends of the transducer extension rod and configured for stabilizing the transducer extension rod.

17. A system for non-destructive inspection of a structure, comprising:
- an extension coupler comprising an extendable and retractable distal end; and
- an inspection probe attached to the distal end of the extension coupler, configured for traveling over holes and off edges of the structure, and comprising at least one pulse echo ultrasonic transducer configured for inspecting the structure as the inspection probe and transducer are moved over the structure by the extension coupler,
- wherein the extension coupler is configured to extend and retract the first end to which the inspection probe is attached for applying pressure to the inspection probe to press the inspection probe against the structure, and wherein the extension coupler is configured to temporarily lock the extended or retracted position of the inspection probe with respect to the extension coupler when the inspection probe passes over one or more of the edge of the hole, over the hole, over the edge of the structure, and past the edge of the structure, thereby preventing the inspection probe from extending past the surface of the structure into the hole or off the edge of the structure by the pressure applied to the inspection probe by the extension coupler.

18. The system of claim 17, wherein the extension coupler comprises:
- a dual action cylinder having an extendable and retractable cylinder piston rod having a first end protruding from the dual action cylinder;
- a transition rod connected to the protruding first end of the cylinder piston rod for translating the motion of the cylinder piston rod, the transition rod having a first end connected to the protruding distal end of the cylinder piston rod and a second end; and
- a transducer extension rod connected to the second end of the transition rod for translating the motion of the transition rod and the cylinder piston rod, the transducer extension rod having a first end connected to the second end of the transition rod and a second end forming the distal end of the extension coupler.

19. The system of claim 18, wherein the extension coupler further comprises a pillow block bearing surrounding a portion of the transducer extension rod between the first and second ends of the transducer extension rod and configured for stabilizing the transducer extension rod.

20. The system of claim 17, wherein the inspection probe comprises:
- a frame configured for attaching to the second end of the extension coupler and for supporting the transducer;
- at least one sled appendage configured for supporting the frame while traveling over a surface of the structure and rotatably connected to the frame; and
- a braking system capable of affixing the respective positions of the frame and sled appendage in at least a first direction of motion about a first axis defined by the rotatable connection of the frame and the sled appendage.

* * * * *

UNITED STATES PATENT AND TRADEMARK OFFICE
CERTIFICATE OF CORRECTION

PATENT NO.        : 7,640,810 B2    Page 1 of 1
APPLICATION NO.   : 11/178584
DATED             : January 5, 2010
INVENTOR(S)       : Kennedy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 789 days.

Signed and Sealed this

Sixteenth Day of November, 2010

David J. Kappos
*Director of the United States Patent and Trademark Office*